US012582765B2

(12) United States Patent
Pizzochero et al.

(10) Patent No.: US 12,582,765 B2
(45) Date of Patent: Mar. 24, 2026

(54) PUMP WITH PUMPING CHAMBER CREATED BY TELESCOPING ACTION DRIVEN BY FRICTION

(71) Applicant: Becton, Dickinson and Company, Franklin Lakes, NJ (US)

(72) Inventors: Alessandro Pizzochero, Chelmsford, MA (US); Mark Wood, Sterling, MA (US); Russell Cole, River Vale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 829 days.

(21) Appl. No.: 17/795,811

(22) PCT Filed: Jan. 20, 2021

(86) PCT No.: PCT/US2021/014096
§ 371 (c)(1),
(2) Date: Jul. 27, 2022

(87) PCT Pub. No.: WO2021/154555
PCT Pub. Date: Aug. 5, 2021

(65) Prior Publication Data
US 2023/0067085 A1      Mar. 2, 2023

Related U.S. Application Data

(60) Provisional application No. 62/968,576, filed on Jan. 31, 2020.

(51) Int. Cl.
*A61M 5/142*          (2006.01)

(52) U.S. Cl.
CPC .... *A61M 5/14248* (2013.01); *A61M 5/14216* (2013.01); *A61M 5/1422* (2013.01); *A61M 2202/0486* (2013.01)

(58) Field of Classification Search
CPC .......... A61M 5/14248; A61M 5/14216; A61M 5/1422; A61M 2202/0486; G01F 11/027; G01F 11/029
See application file for complete search history.

(56) References Cited

U.S. PATENT DOCUMENTS 10,512,719 B2 * 12/2019 Focht ................ A61M 5/14216
2005/0277883 A1   12/2005 Kriesel
(Continued)

FOREIGN PATENT DOCUMENTS

CN      204995910 U      1/2016
JP      2015-205175 A    11/2015
JP      2017-513577 A    6/2017

OTHER PUBLICATIONS

International Search Report dated Apr. 2, 2021, which issued in the corresponding PCT Patent Application No. PCT/US2021/014096.
(Continued)

*Primary Examiner* — James D Ponton
(74) *Attorney, Agent, or Firm* — Dickinson Wright PLLC

(57) ABSTRACT

A pump subsystem for fluid delivery (e.g., in a wearable patch pump) is provided wherein pumping action is generated by linear piston movement that pulls a plug, which is interconnected to the piston between two mechanical extremes or end stops in a telescopic or variable volume fluid chamber. Such interconnection enables piston and plug to move a certain distance with respect to each other that corresponds to a predefined swept volume of the pump subsystem. Telescoping-like effect of relative piston and plug movement provides for intake and discharge of fluid with respect to the fluid chamber. Movement of plug within piston can be enabled by the friction of seals placed on the plug, which serve to provide resistance to piston motion and therefore force translation motion of the plug to lag relative
(Continued)

to the piston translation motion during portions of the pump cycle.

9 Claims, 17 Drawing Sheets

(56) References Cited

U.S. PATENT DOCUMENTS

| | | | | |
|---|---|---|---|---|
| 2009/0093792 | A1 | 4/2009 | Gross et al. | |
| 2009/0198215 | A1 | 8/2009 | Chong et al. | |
| 2014/0276537 | A1* | 9/2014 | Kruse | A61M 5/14244 |
| | | | | 604/500 |
| 2017/0080157 | A1 | 3/2017 | Cabiri et al. | |
| 2018/0272057 | A1 | 9/2018 | Focht et al. | |
| 2019/0344010 | A1 | 11/2019 | Pizzochero et al. | |

OTHER PUBLICATIONS

Australian Examination Report dated Aug. 19, 2025, which issued in the corresponding Australian Patent Application No. 2021212614.

* cited by examiner

PUMP WITH PUMPING CHAMBER CREATED BY TELESCOPING ACTION DRIVEN BY FRICTION

BACKGROUND

Field

Illustrative embodiments relate generally to pump sub-systems for use in wearable medication infusion patches.

Description of Related Art

Diabetes is a group of diseases marked by high levels of blood glucose resulting from defects in insulin production, insulin action, or both. Diabetes can lead to serious health complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of Type 1 diabetes. The first mode includes syringes and insulin pens that require a needle stick at each injection, typically three to four times per day. These devices are simple to use and relatively low in cost. Another widely adopted and effective method of treatment for managing diabetes is the use of an insulin pump. Insulin pumps can help users keep their blood glucose levels within target ranges based on their individual needs, by providing continuous infusion of insulin at varying rates to more closely mimic the behavior of the pancreas. By using an insulin pump, users can match their insulin therapy to their lifestyles, rather than matching their lifestyles to how an insulin injection is working for them.

However, conventional insulin pumps suffer from several drawbacks. For example, lead screw and piston type pump sub-systems typically used in insulin pumps are often cumbersome to users, requiring a large height and a large a footprint for a wearable insulin pump.

Conventional insulin pumps also typically require a large number of components and moving parts, thereby increasing risks of mechanical failure.

Conventional insulin pumps also typically have valves that are prone to leaking at elevated system back pressures. This can result in reduced dose accuracy and reliability.

Conventional insulin pumps also typically require large working volumes and large system volumes exposed to potentially high back pressure. This can result in reduced dose accuracy and reliability.

SUMMARY

The above and other problems are overcome, and additional advantages are realized, by illustrative embodiments.

Another aspect of illustrative embodiments is to provide a pump sub-system with no direct fluid path between the reservoir and the cannula, compared to conventional pump sub-systems, thereby better safeguarding a user against overdose.

Another aspect of illustrative embodiments is to provide a pump sub-system with a small working volume and a low system volume exposed to potentially high back pressure, compared to conventional pump sub-systems, thereby increasing; accuracy and reliability of pumps such as insulin patches.

In accordance with illustrative embodiments, a fluid delivery device is provided that comprises a housing; a piston configured to be controllably translated within the housing; and a plug having a distal end thereof connected to a proximal end of the piston, the plug being configured to translate within the housing. The proximal end of the piston is configured with a region therein that defines a telescopic fluid chamber in which the distal end of the plug can translate relative to the piston to permit fluid to flow into the fluid chamber and to discharge fluid from the fluid chamber.

In accordance with aspects of the illustrative embodiments, the housing comprises a reservoir port through which fluid is introduced into the housing and a patient port through which fluid is discharged from the housing.

In accordance with aspects of the illustrative embodiments, the piston is controllably translated to align the fluid chamber with the reservoir port during an intake operation of the fluid delivery device, and to align the fluid chamber with the patient port during a discharge operation of the fluid delivery device.

In accordance with aspects of the illustrative embodiments, the plug is configured with a frictional engagement relative to the housing that provides an amount of friction to cause translation of the plug to lag relative to the piston until the amount of friction is overcome by translation of the piston.

In accordance with aspects of the illustrative embodiments, the distal end of the plug translates between two end stop positions within the piston region, when the distal end of the plug reaches one of the two end stop positions, the amount of friction is overcome and the plug translates with the piston relative to the housing.

In accordance with aspects of the illustrative embodiments, the fluid delivery device further comprises an interlock mechanism between the housing and the piston comprising an arcuate cam slot in one of the housing and the piston, and a pin on the other one of the housing and the piston that is configured to engage with the cam slot. When the piston is rotated, the cam slot is configured to control a distance along which the piston translates relative to the housing.

In accordance with aspects of the illustrative embodiments, the plug and the piston are each provided with a seal, and the respective seals are configured to confine fluid in the fluid chamber between the seals.

In accordance with aspects of the illustrative embodiments, the plug is configured with a frictional engagement relative to the housing that provides an amount of friction to cause translation of the plug to lag relative to the piston until the amount of friction is overcome by translation of the piston, and the seal on the piston is configured to contribute to the amount of friction.

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims.

BRIEF DESCRIPTION OF THE DRAWINGS

The above and/or other aspects and advantages of embodiments of the illustrative embodiments will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1:
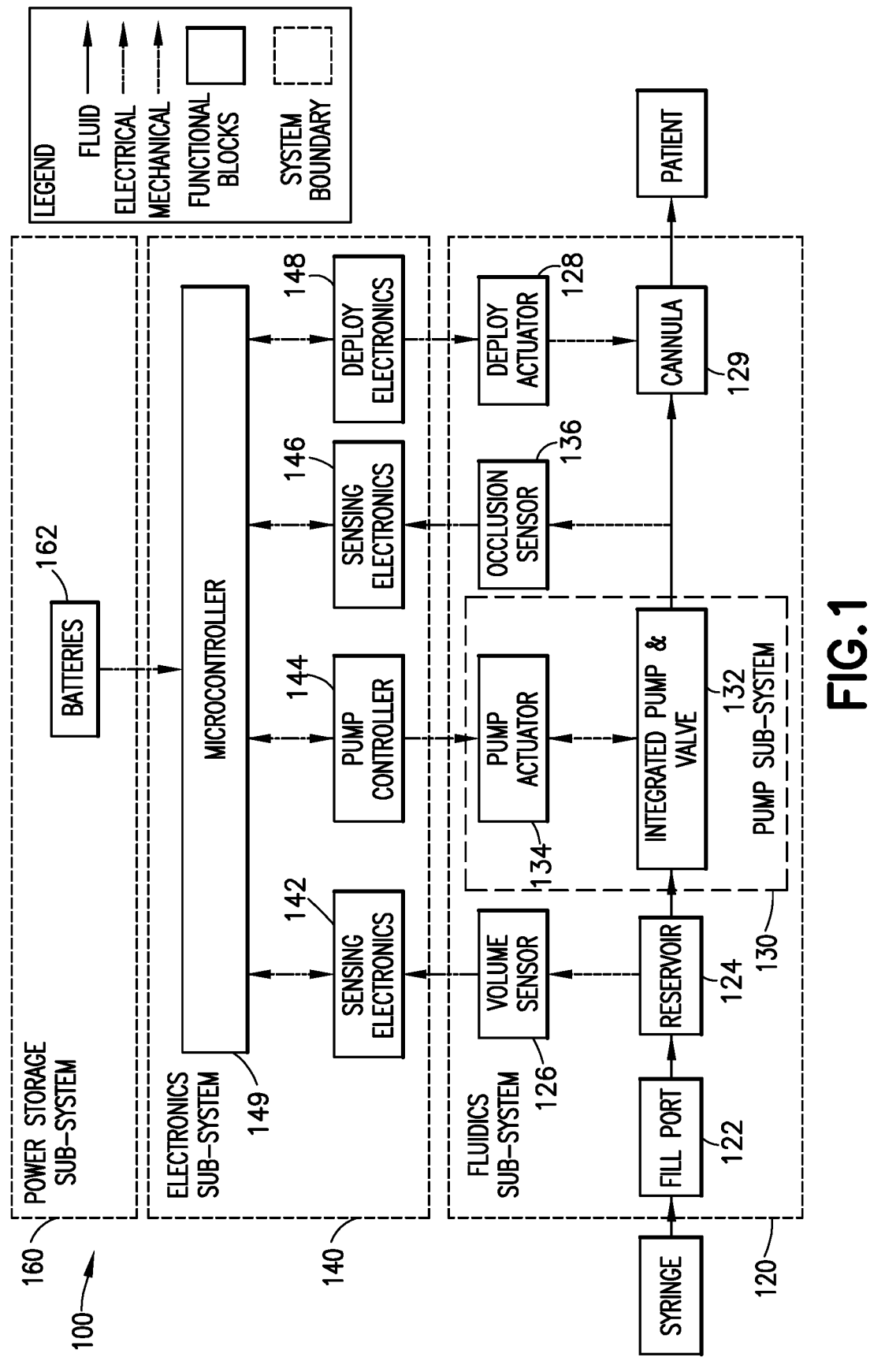
FIG. 1 shows a diagram of an architecture of an illustrative embodiment of a patch pump.

As will be appreciated by one skilled in the art, there are numerous Nays of carrying out the examples, improvements, and arrangements of a pump in accordance with embodiments disclosed herein. Although reference will be made to the illustrative embodiments depicted in the drawings and the following descriptions, the embodiments disclosed herein are not meant to be exhaustive of the various alternative designs and embodiments that are encompassed by the disclosed technical solutions, and those skilled in the art will readily appreciate that various modifications may be made, and various combinations can be made with departing from the scope of the disclosed technical solutions.

Although various persons, including, but not limited to, a patient or a healthcare professional, can operate or use illustrative embodiments of the present disclosure, for brevity an operator or user will be referred to as a "user" hereinafter.

Although various fluids can be employed in illustrative embodiments of the present disclosure, for brevity the liquid in an injection device will be referred to as "fluid" hereinafter.

Illustrative embodiments are depicted in FIGS. 1 through 18L. In an illustrative embodiment, a pump sub-system is provided for use in a wearable insulin infusion patch;

however, as stated above, the wearable infusion patch can be used to deliver other types of fluids such as a medicament other than insulin. For example, in illustrative embodiments of the present disclosure, the pump sub-system is part of a larger fluidics sub-system that includes a reservoir for storing insulin and a cannula assembly for delivering the insulin into sub-cutaneous tissue. The pump subsystem draws a small dose of fluid from the reservoir and then pushes it down the cannula line and into the patient. The fluid dose is small relative to the reservoir volume, such that many pump strokes are required to completely empty the reservoir.

FIG. 1 shows a diagram of an architecture of a patch-type pump 100 in accordance with an exemplary embodiment of the present disclosure. The patch pump 100 includes a fluidics sub-system 120, an electronics sub-system 140 and a power storage sub-system 160.

The fluidics sub-system 120 includes a fill port 122 in fluid communication with a reservoir 124. The reservoir 124 is adapted to receive fluid from a syringe, through the fill port.

The fluidics sub-system 120 further includes an optional volume sensor 126 coupled to the reservoir 124. The volume sensor 126 is adapted to detect or determine the fluidic volume of the reservoir.

The fluidics sub-system 120 further includes a pump sub-system 130, which includes an integrated pump and valve system 132 mechanically coupled to a pump actuator 134. The integrated pump and valve system 132 is in fluid communication with the reservoir 124 of the fluidics sub-system 120, and is actuated by the pump actuator 134.

The fluidics sub-system 120 further includes a cannula mechanism having a deployment actuator 128 mechanically coupled to a cannula 129. The deployment actuator 128 is adapted to insert the cannula 129 into a user. The cannula 129 is in fluid communication with the integrated pump and valve system 132 of the pump sub-system 130.

The fluidics sub-system 120 further includes an optional occlusion sensor 136 coupled to a fluid pathway between the cannula 129 and the integrated pump and valve system 132. The occlusion sensor 136 is adapted to detect or determine an occlusion in the pathway between the cannula 129 and the integrated pump and valve system 132.

The electronics sub-system 140 includes optional volume sensing electronics 142 electrically coupled to the volume sensor 126 of the fluidics sub-system 120, a pump controller 144 electrically coupled to the pump actuator 134 of the pump sub-system 130, optional occlusion sensing electronics 146 electrically coupled to the occlusion sensor 136 of the fluidics sub-system 120, and optional deployment electronics 148 electrically coupled to the cannula 129 of the fluidics sub-system (e.g., the cannula deployment actuator 128 can be manual). The electronics sub-system 140 further includes a microcontroller 149 electrically coupled to the volume sensing electronics 142, the pump controller 144, the occlusion sensing electronics 146, and the deployment electronics 148.

The power storage sub-system 160 includes batteries 162 or any other electrical power source known in the art. The batteries 162 can be adapted to power any element or electronic component of the patch pump 100.

Figure 2:
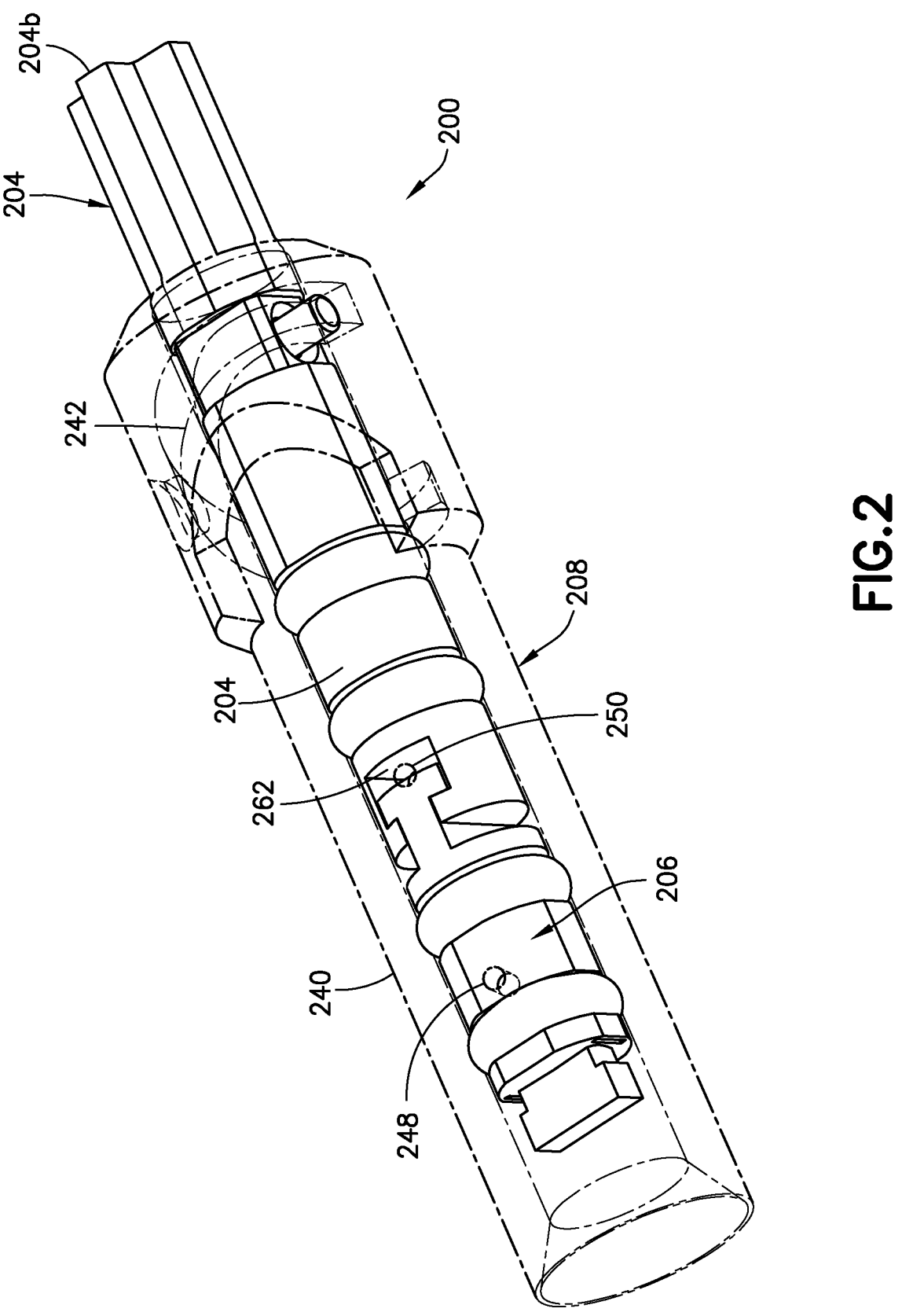
FIG. 2 is a perspective view of an example pump sub-system in accordance with an illustrative embodiment.
Figure 3:
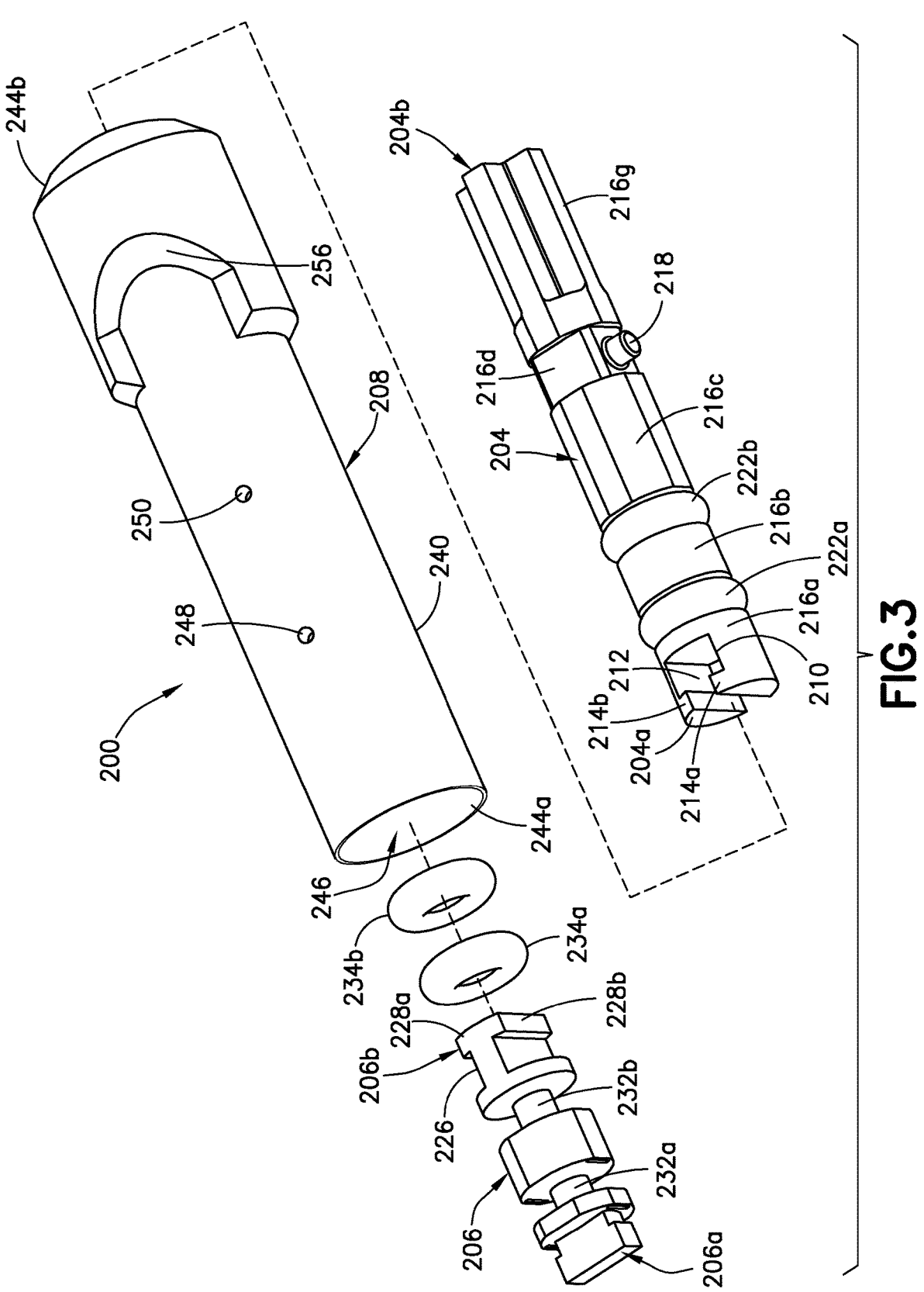
FIG. 3 is an exploded view of the example pump sub-system in FIG. 2.

FIG. 2 is a perspective view of an example pump sub-system 200 in accordance with an illustrative embodiment. FIG. 3 is an exploded view of the example pump sub-system 200. The pump sub-system 200 has a pump housing 208, and an interconnected piston 204 and plug 206 that are controllably and selectively translated and rotated within the pump housing by a pump actuator 134 connected to the piston 204.

Figure 4:
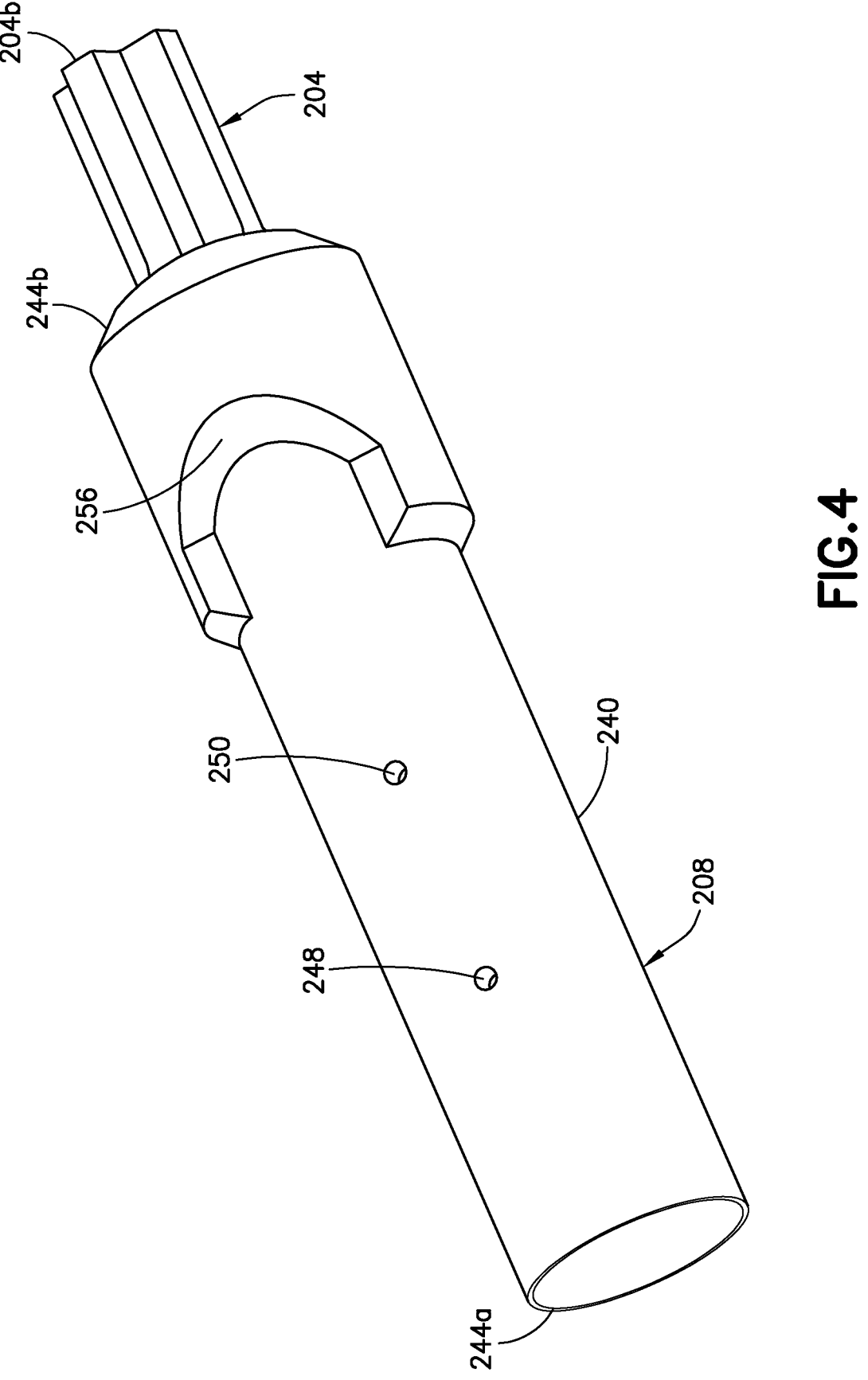
FIGS. 4 and 5 are partial perspective views of the example pump sub-system in FIG. 2.

For example, the pump actuator 134 can be a gearbox not shown in FIGS. 2 through 4. An example of a gearbox is described in commonly-owned WO 2015/157174 which is incorporated herein by reference.

With reference to FIGS. 2 through 7, the pump housing 208 is generally configured as a tubular member with an outer wall 240 forming a cylindrical or tubular shape defining an internal space 246 dimensioned to receive the piston 204 and the plug 203 therein. The outer circumferences of the piston 204 and the plug 206 are dimensioned to allow a volume of reservoir fluid into an annular region 260 defined between the piston 204 outer wall and the inner surface of the wall 240 of the pump housing 208 and between the plug 206 outer wall and the inner surface of the wall 240 of the pump housing 208. As described below, seals are provided to define a telescopically movable pump chamber 262 using a portion of the annular region 260 within the pump housing 208. Portions of the piston 204, and/or the plug 206 and/or the internal surface of the wall 240 of the pump housing 208 can have flat sections or indents to increase the volume of fluid in the annular region 260.

Figure 5:
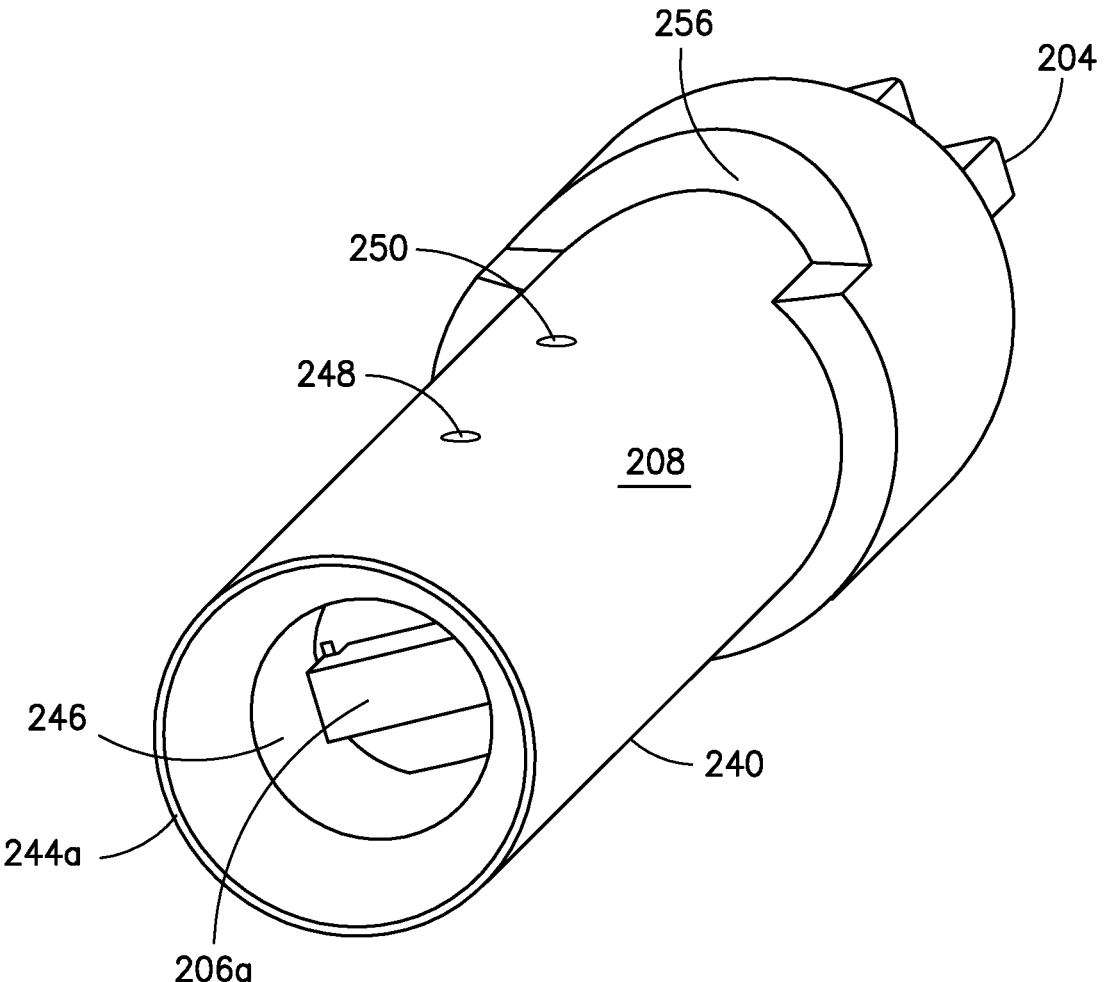
Figure 6:
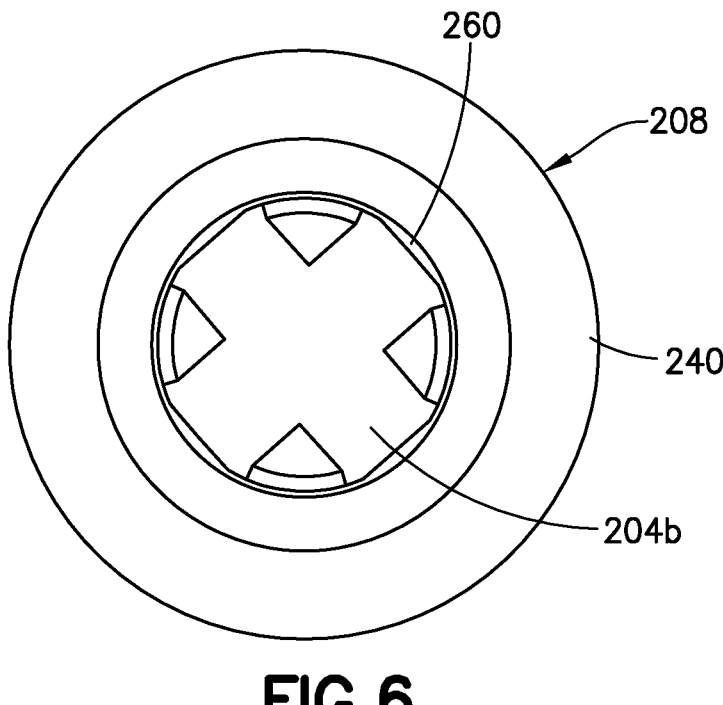
FIGS. 6 and 7 are distal and proximal end views, respectively, of the example pump sub-system in FIG. 2.
Figure 7:
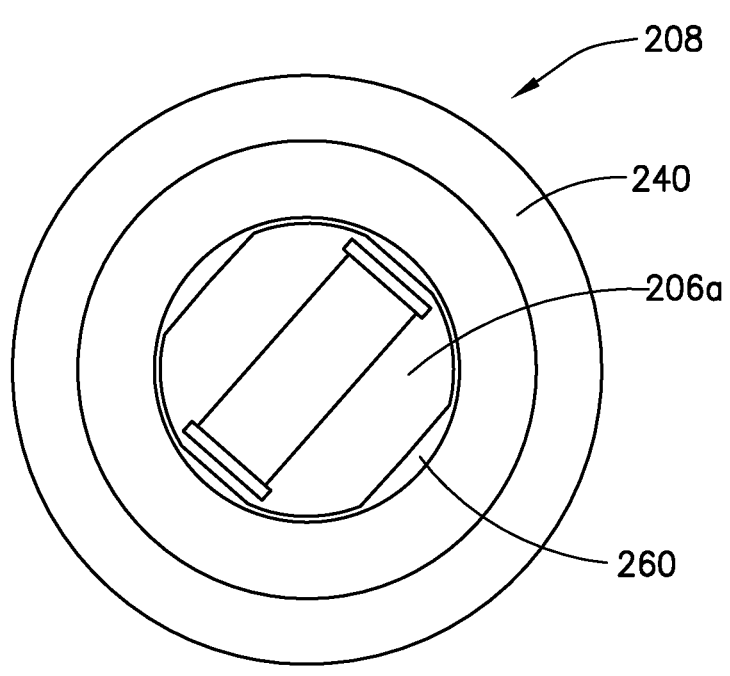
Figure 8:
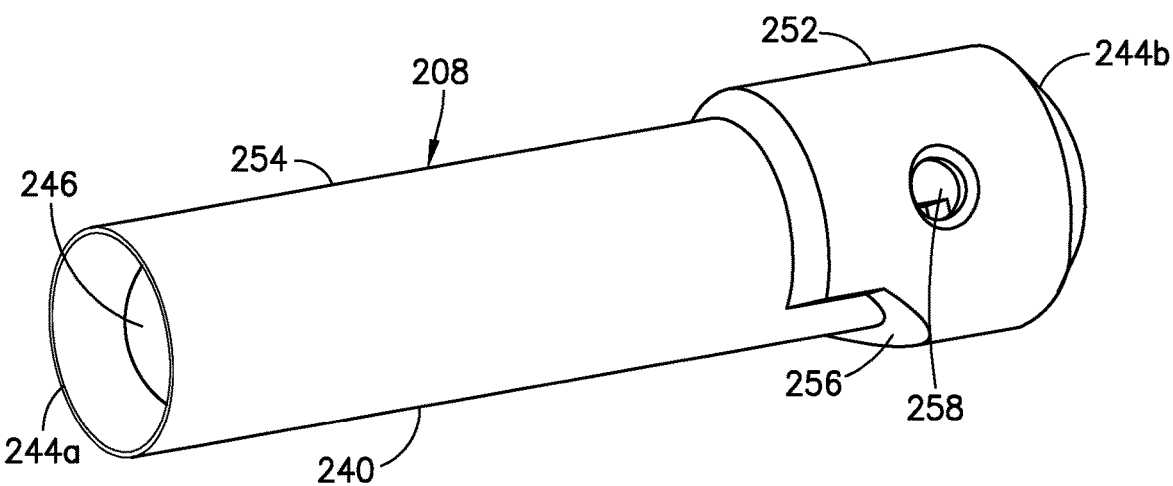
FIGS. 8 and 9 are perspective views of a housing in the example pump sub-system in FIG. 2.
Figure 9:
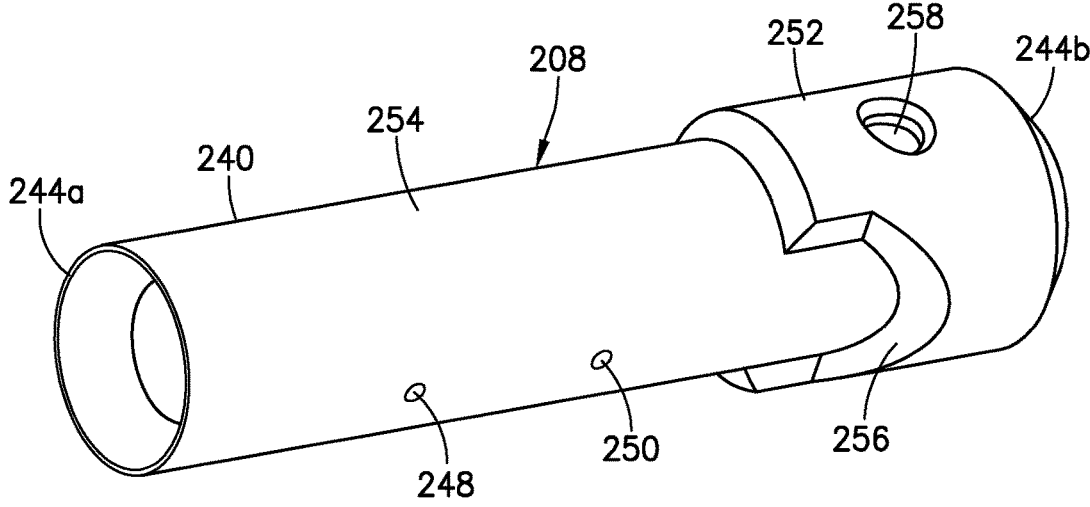

FIG. 4 is a perspective view of the pump housing 208 showing a portion of the piston 204 extending from the distal end 244 thereof, and FIGS. 5, 8 and 9 are additional perspective views of the pump housing 208. The exterior of the pump housing 208 has a portion 252 with larger circumference than the portion 254 that has ports 248 and 250 described below. The portion 252 of the pump housing is provided with an internal cam slot 242 described below that operates as an interlock mechanism, a notch 256 configured to facilitate interfacing with the baseplate of the pump during assembly and lessen profile of the pump, and an aperture 258 to facilitate assembly of the pin 218. FIGS. 6 and 7 are cross-section views of the pump housing 208 at respective ends thereof, showing the plug 206 at one end (i.e. FIG. 7), the piston 204 at the other end (i.e., FIG. 6) and the annular region 260. It is to be understood that the pump housing 208 can be a shape other than a cylinder and that the shape and the exterior circumference and interior diameter can vary along the longitudinal axis of the pump housing 208.

The outer wall 240 is formed with a reservoir port 248 that extends from the internal space 246 of the pump housing 208 and through the outer wall 240 for fluid connection from the pump housing 208 to the reservoir 124 via a fluid pathway (not shown) in the patch pump 100. The outer wall 240 is also formed with a patient port 250 that extends from the internal space 246 of the pump housing 208 and through the outer wall 240 for fluid connection from the pump housing 208 to the cannula 129 via a fluid pathway (not shown) in the patch pump 100. The pump housing 208 has a distal end 244b that receives the piston 204 as illustrated in FIG. 2. The distal end 204b of the piston 204 can be connected to a gearbox or other device 134 that controllably moves the piston 204 and plug 206 within the pump housing 208 to receive fluid within the pump chamber 262 (e.g., via the reservoir port 248) and to expel fluid from the pump chamber 262 (e.g., via the patient port 250).

The piston 204 will now be described with reference to FIGS. 11, 12, 13 and 14. The piston 204 has a distal end 204b engaged by a gearbox or other device 134 (not shown). The distal end 204b of the piston 204 can be provided with longitudinal ribs that facilitate mechanical engagement or grip by the gearbox. The proximal end 204a of the piston 204 is engaged with a distal end 206b of the plug 206. The proximal end 204a of the piston 204 is configured with a notch region 210 dimensioned to receive the distal end 206b of the plug 206 and allow the distal end 206b of the plug to move relative to the piston 204 within the notch region 210 when a pin 218 follows a cam slot 242 in the pump housing 208 as described below in connection with an interlock mechanism. The notch region 210 comprises an opening 212 to receive the distal end 206b of the plug 206 and flanges 214a,b to hold a neck 226 of the plug 206.

The piston 204 and plug 206 engagement in the notch region 210, and a surrounding annular region 260 within the pump housing 208 enclosed by two seals described below, define the movable or translating pump chamber 262 to which the ports 248 and 250 are exposed. The piston 204 is translated by a gearbox or other device 134 in a manner described in more detail below to create a telescopic effect wherein the notch region 210, and a portion of the annular region 260 that lies between two seals, facilitate performance of intake and discharge strokes during a pump cycle.

The piston 204 can have one or more sections 216a, b, c, d having outer circumference(s) dimensioned to allow a volume of reservoir fluid in the annular region 260 defined between piston 204 outer wall and the inner wall of the pump housing 208. The section 216a with the proximal end 204a of the piston 204 can have areas about its periphery that are flat or indented relative to other areas about its periphery to increase the volume of the annular region 260 between the piston 204 outer wall and the inner wall of the pump housing 208. The piston 204 also has sections 216 d,e,f that are interspersed between respective sections 216a, b, c, g and that have lesser circumference(s) than the outer circumferences, including two seal sections 216 e,f and a pin coupling section 216d.

Figure 10:
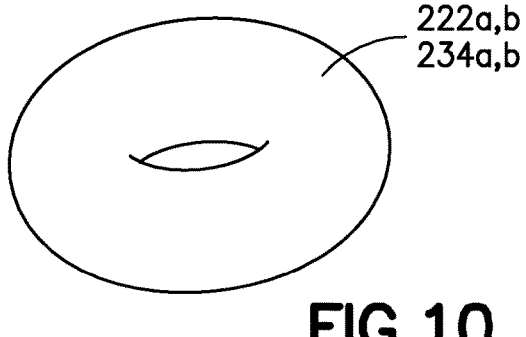
FIG. 10 is a perspective view of an example seal in the example pump sub-system in FIG. 2.
Figures 11, 12:
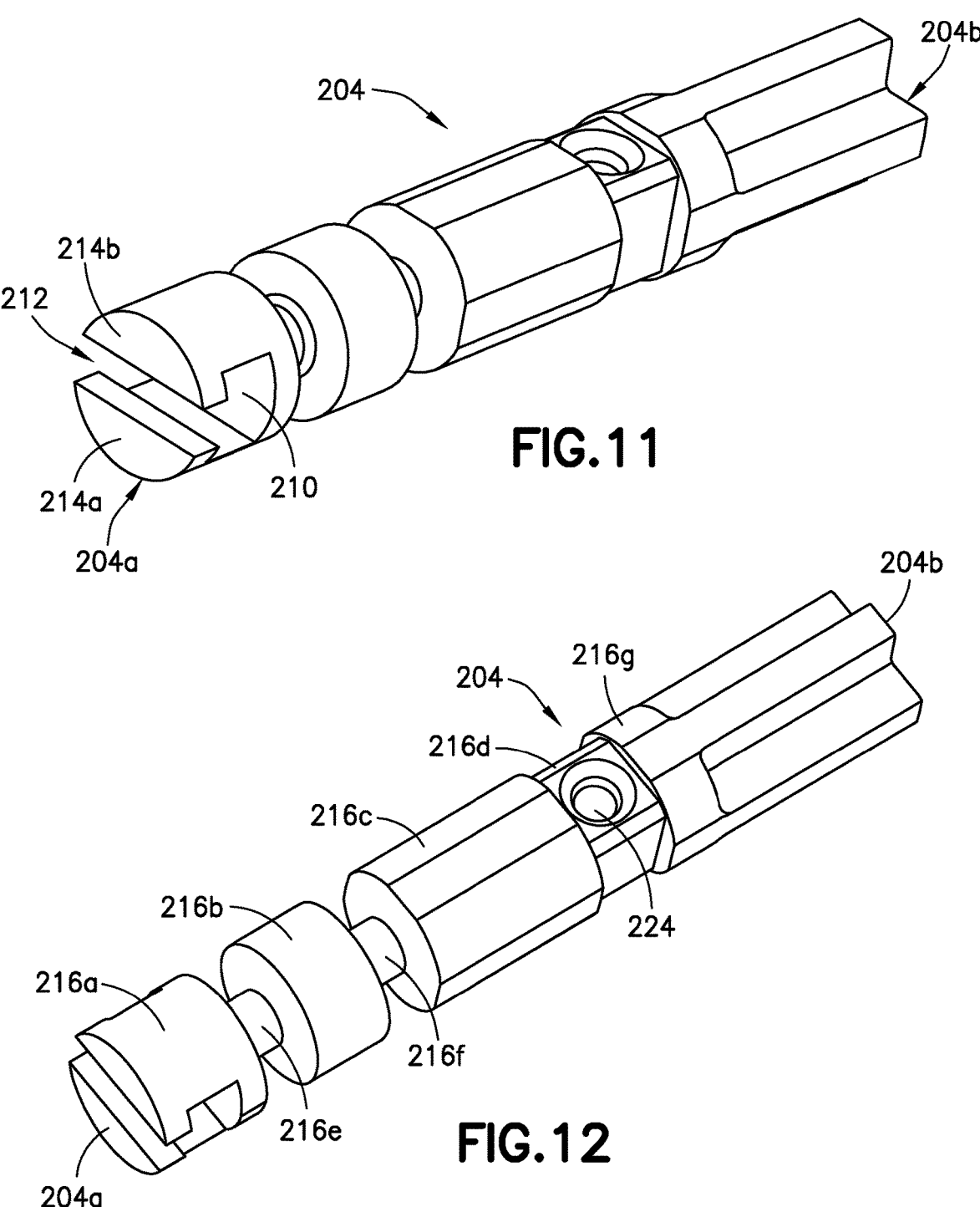
FIGS. 11 and 12 are perspective views of a piston in the example pump sub-system in FIG. 2.
Figures 13, 14:
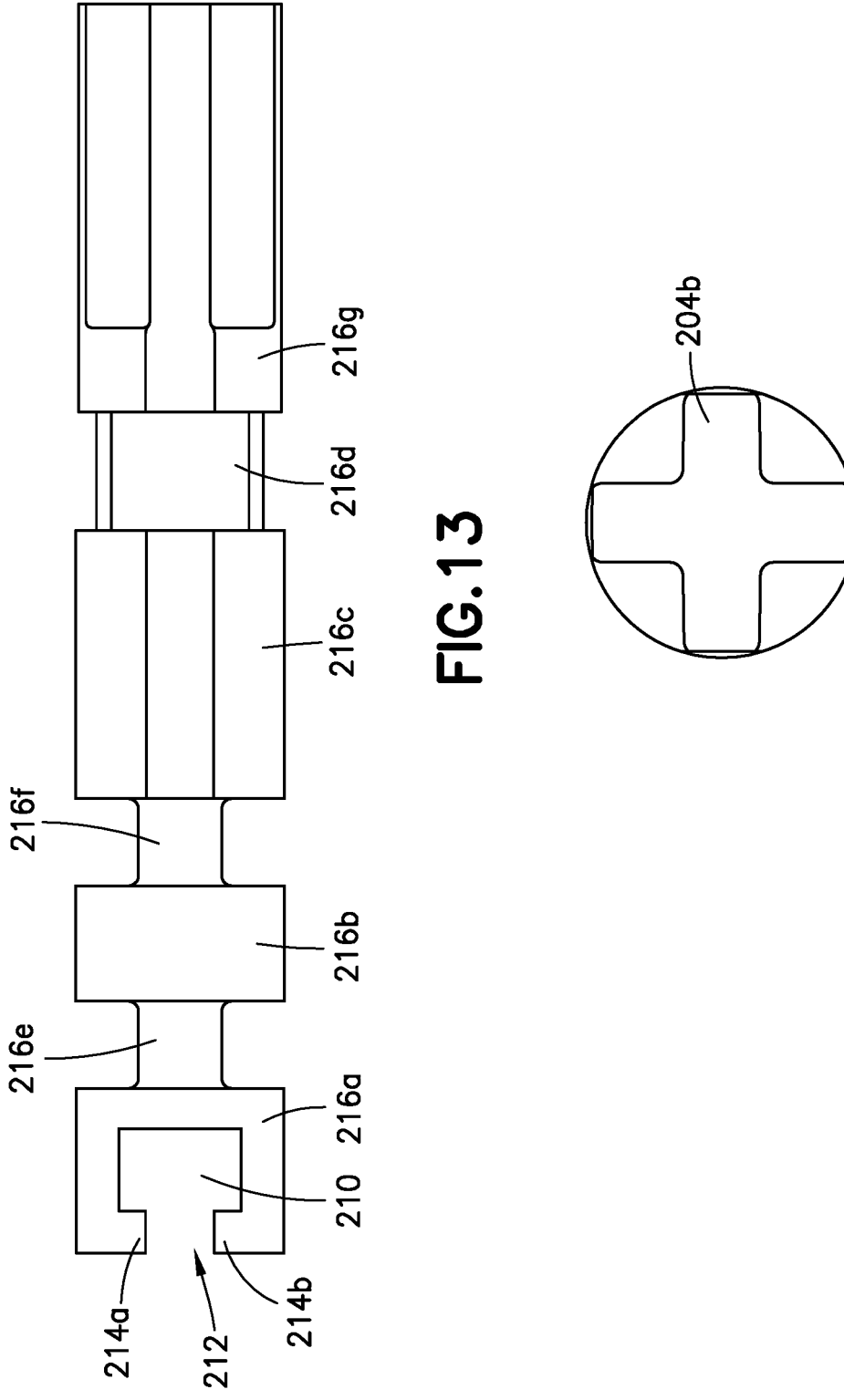
FIG. 13 is a side view of the piston in FIGS. 11 and 12.
FIG. 14 is distal end view of the piston in FIGS. 11, 12 and 13.

The seal sections 216 e,f are each dimensioned to receive a seal such as the corresponding seal 222a,b depicted in FIGS. 3 and 10. The seals 222a,b can each be, for example, an O-ring configured to have an outer circumference dimensioned to fill portions of the annular region 260 that surround the sections 216 e,f of the piston and thereby provide a pressure fit against the inner wall of the pump housing 208 within these portions that is sufficient to (1) prevent leakage of any fluid into these portions 260a,b; yet (2) also allow the seals to slide along the longitudinal axis of the pump housing 208 when the piston 204 is controllably translated by the gearbox or other device. The interlock mechanism described herein also involves rotation of the piston and plug as well as their translation. The seals 222a,b are configured such that the piston 204 rotates within the O-rings used as the seals 222a,b and relative thereto such that the seals 222a,b do not rotate with the piston 204. The torque balance can be such that the torque from the housing is greater than the torque within the seal glands, thus leading to relative movement of the piston with respect to the 222a,b seals. Sometimes, depending on actual friction values, particularly when the seals are wetted by the fluid, the torque balance nay change. Regardless, pump functionality when sealing function is maintained. The piston 204 supports a pin 218 in the pin coupling section 216d that follows a cam slot 242 in the pump housing 208. For example, the section 216d can be provided with an aperture 224 to receive the pin 218 which can be press fit, glued, molded or otherwise fastened to the aperture 224 or otherwise molded to a part of the section 216d without need for an aperture 224.

The plug 206 will now be described with reference to FIGS. 3, 15, 16 and 17. The plug 206 has a proximal end 206a, and a distal end 206b that engages with the proximal end 204a of the piston 204. The distal end 206b of the plug 206 has a neck 226 and flanges 228a,b. The neck 226 is dimensioned to be slidably received within the opening 212 of the notch region 210 of the piston 204, and to have a length that extends sufficiently along the longitudinal axis of the pump sub-system to translate flanges 214a,b provided on the end of the neck 226 within the notch region 210. It is to be understood that different shapes and dimensions can be used for the distal end 206b of the plug 206 and the proximal end 204a of the piston 204 to provide a moveable or translating engagement of the piston 204 relative to the plug 206 within the notch region 210 of the movable or translating pump chamber 262.

Figures 15, 16:
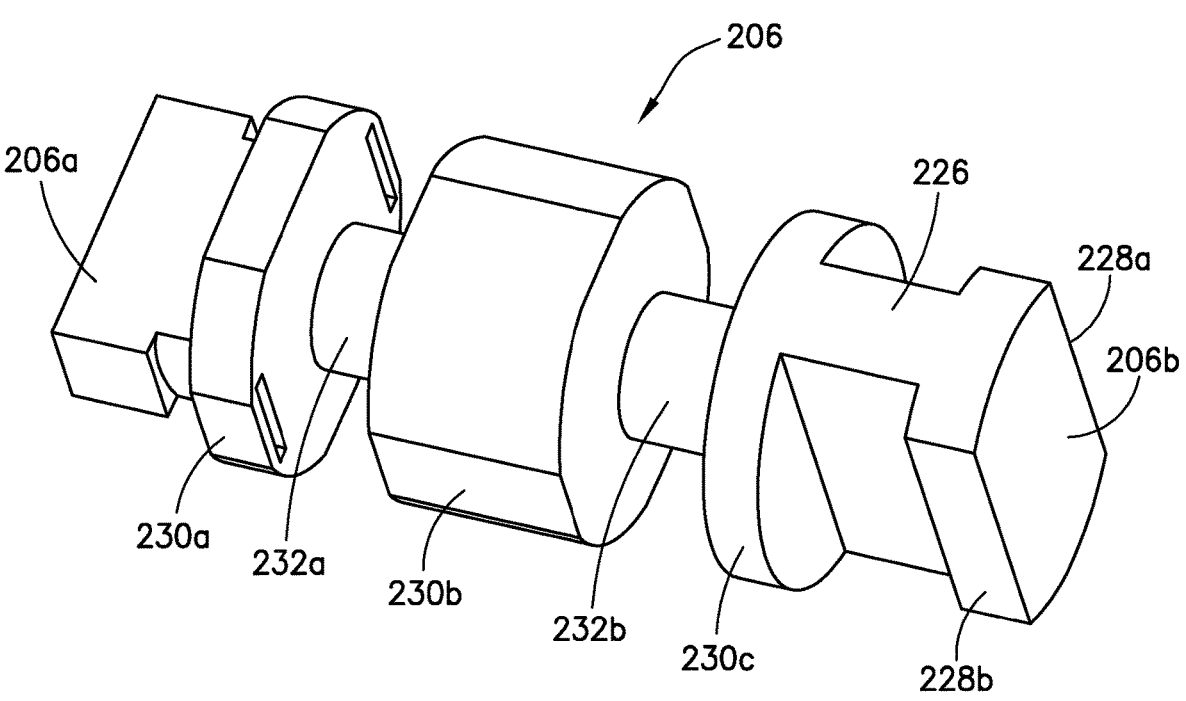
FIGS. 15 and 17 are perspective views of a plug in the example pump sub-system in FIG. 2.
FIG. 16 is a side view of the plug in FIGS. 15 and 17.
Figure 17:
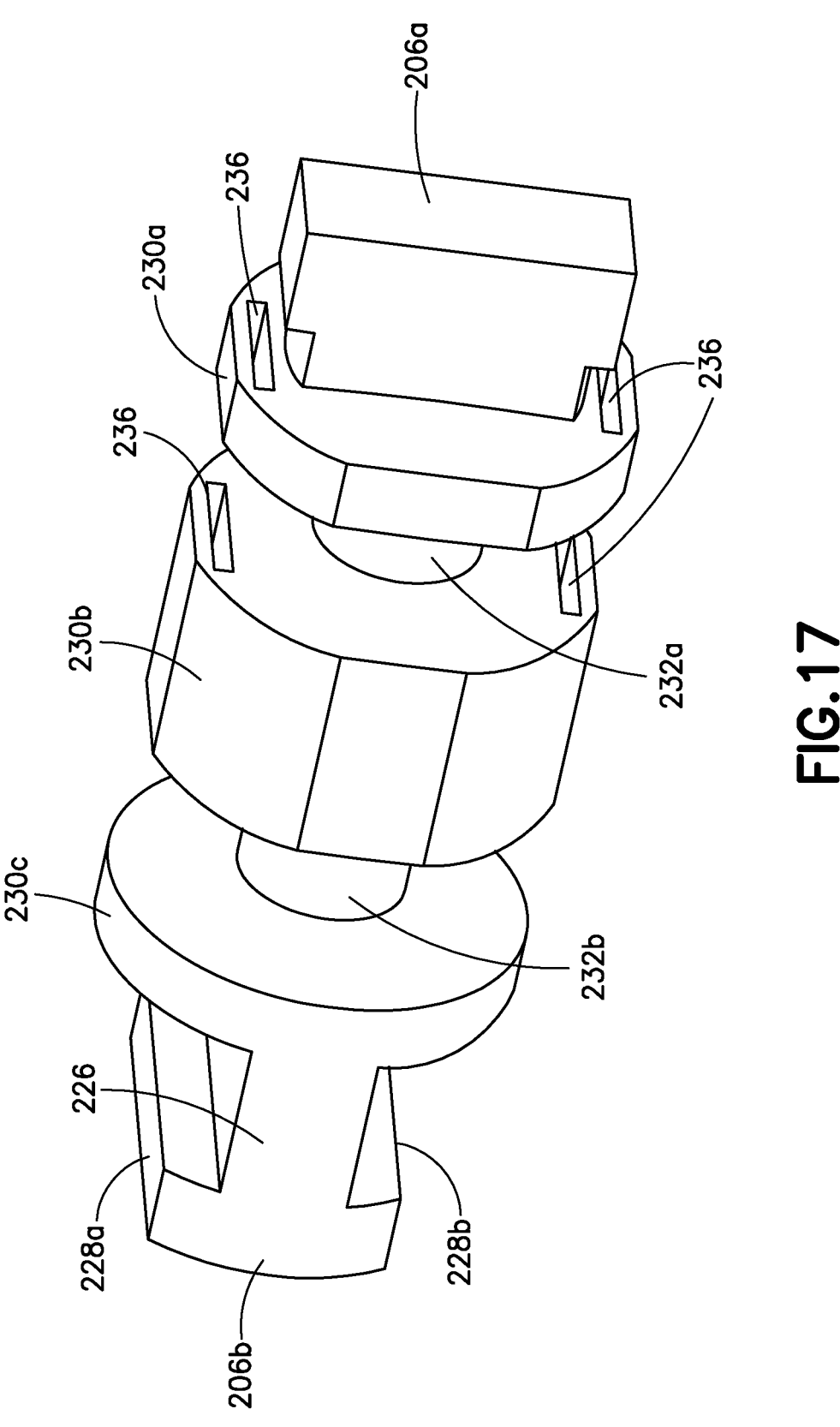

With continued reference to FIGS. 15, 16 and 17, the plug 206 has three sections 230a,b,c with outer circumference(s) dimensioned to allow a volume of reservoir fluid in the annular region 260 defined between plug 206 outer wall and the inner wall of the pump housing 208. The section 230c with the distal end 206b of the plug 206 can have areas about its periphery that are flat or indented relative to other areas about its periphery to increase the volume of the annular region 260 between the piston 204 outer wall and the inner wall of the pump housing 208. The plug 206 also has two seal sections 232a,b that are interspersed between respective sections 230a,b,c and that have lesser circumference(s) than the outer circumferences. The seal sections 232a,b are each dimensioned to receive a seal such as the corresponding seal 234a,b depicted in FIGS. 3 and 10. The seals 234a,b can be configured similarly as the seals 222a,b. For example, the seals 234a,b can be dimensioned similarly to the seals 222a,b with respect to the outer wall of the pump housing and provide a friction fit. The seals 234a,b can also be dimensioned such that the plug 206 rotates with respect to the 234a,b. The seals 234a,b and 222a,b can be O-rings made of Butyl rubber, for example. The seals are designed to have drug compatibility and desirable mechanical function (e.g., sizing, compression set, friction, and so on). The distal seal 234b of the plug 206 and the proximal seal 222a of the piston 204 seal reservoir fluid within the moveable or translating pump chamber 262 from the remaining portion of the annular region 260 that does not coincide with the pump chamber 262.

With continued reference to FIGS. 3 through 10, the distal section of the pump housing 208 is configured with an interlock mechanism that includes a can slot 242 formed in the internal surface of the outer wall 240 that receives and guides the pin 218 provided on the piston 204. The length of the can slot 242 and the degree of curvature along its length depends on a designated distance that the piston 204 travels along the longitudinal axis of the pump housing 208 to controllably align the reservoir port 248 between two seals (i.e., seal 234b of the plug 206 and seal 222a of the piston 204) for an intake stroke of a pump cycle that draws fluid from the reservoir 124 into the internal space 246 of the of the movable pump chamber 262, to controllably align the patient port 250 between the same two seals 234b and 222a for a discharge stroke that pushes fluid from the movable pump chamber 262 toward the cannula 129, and to controllably rotate the piston during a stroke and reverse direction of rotation for the next stroke (e.g., from clockwise piston 204 rotation to counterclockwise piston 204 rotation, depending on desired phase of a pump cycle). It is to be underwood that the interlock mechanism can comprise a cam slot in the piston 204 that guides a pin on the housing 208.

Operation of the pump sub-system 200 during a full pump cycle comprising a discharge stroke and intake stroke is described herein with reference to FIGS. 18A through 18L in accordance with an illustrative embodiment. As illustrated in FIGS. 18A through 18L, when the pump sub-system 200 is driven by a gearbox or other device, pumping action is generated by linear piston 204 movement that pulls a plug 206 that is interconnected to the piston 204 between two mechanical extremes (e.g., top and bottom surfaces of the flanges 228a,b on the distal end of the plug 206 engaging respective proximal and distal ends of the notch region 210 in the piston 204), Such interconnection enables the piston 204 and the plug 206 to move a certain distance with respect to each other. This distance corresponds to a predefined swept volume of the pump sub-system 200. Such interconnection provides a "telescoping"-like effect whereby the plug 206 moves within the piston 204 that is enabled by the friction of the seals 234a,b placed on the plug 206, which serve to provide resistance to piston 204 motion and therefore force translation motion of the plug 206 to lag relative to the piston 204's translation motion during portions of the pump cycle described below in connection with FIGS. 18A through 18L.

As described above, the piston 204 is also fitted with seals 222a,b (e.g., O-rings) to prevent leakage of reservoir fluid, but also to stabilize and center the position of the piston 204 during its motion via their spacing along the longitudinal axis of the piston. The piston 204 is driven in rotation by the pin 218 that rides into the cam slot 242 in the pump housing 208.

As described above, the two ports 248, 250 provide connection to the reservoir 124 (e.g., fluid source) and the patient side (e.g. cannula 129), respectively. These port holes 248, 250 are controllably exposed to the movable pump chamber 262 by select positioning of the O-rings 222a,b and 234 a,b along the longitudinal axis of the pump sub-system 200 and sizing of the car slot 242 to move the piston the necessary distances for the corresponding ports 248, 250. When the pump chamber 262 is exposed to the reservoir side (e.g., an intake stroke as described in connection with FIGS. 18A through 18C), the reservoir port 248 is exposed during the motion where the piston 204 is pulled away from the plug 206 and the plug 206 is held back by its O-rings' friction. As the pump chamber 262 is fully extended (e.g., the plug flanges 228a,b engage a proximal wall of the notch region 210), the plug 206 is then pulled with the piston 204 (e.g., FIG. 18D) and the reservoir port 248 is no longer connected to the pump chamber 262. As piston 204 motion continues, the patient side port 250 is exposed to the pump chamber 262 (e.g., as described in connection with FIGS. 18E through 18H).

An example intake stroke during a pump cycle will now be described with reference to FIG. 18A. The pin 218 in the piston 204 is shown at the proximal end 242c of the cam slot 242, and reservoir port 248 is shown exposed to the chamber 262. The piston is rotated (e.g., counterclockwise) and pin 218 glides along section 242a of the slot 242. The plug 206 and piston 204 rotate but there is no translation of either yet.

Figures 18A, 18B:
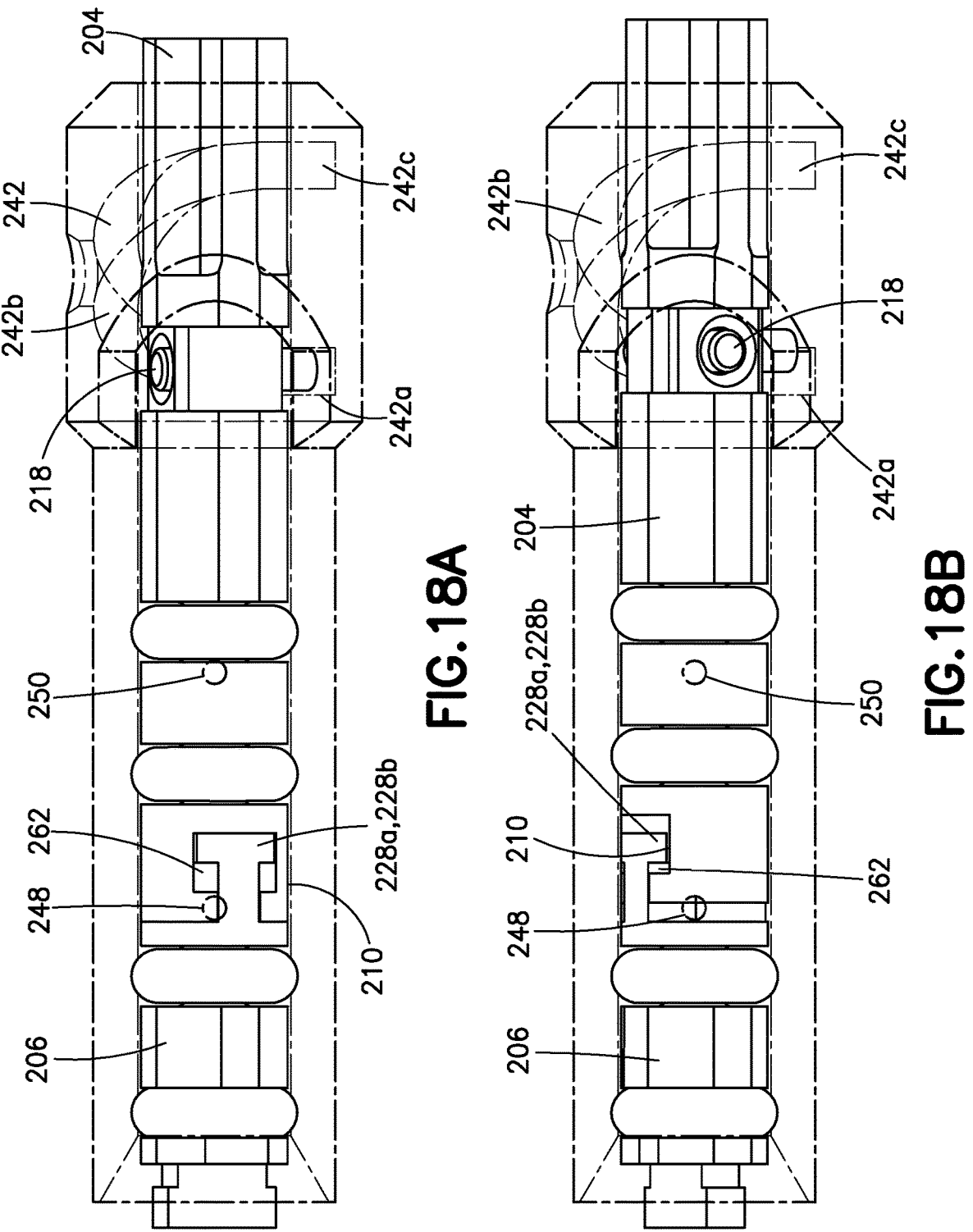
FIGS. 18A, 18B, 18C, 18D, 18E, 18F, 18G, 18H, 18I, 18J, 18K and 18L are side views of the example pump sub-system in FIG. 2 during respective states of a pump cycle in accordance with an illustrative embodiment.

In FIG. 18B, the pin 218 continues along portion 242A of the cam slot 242 and the piston 204 rotates and translates, but the plug does not translate. Its flanges 228a,b pull away from the distal side of the notch region 210 toward the proximal side of the notch region 210 as the piston translates, causing negative pressure in the fluid chamber 262 to pull fluid in through port 248.

Figures 18C, 18D:
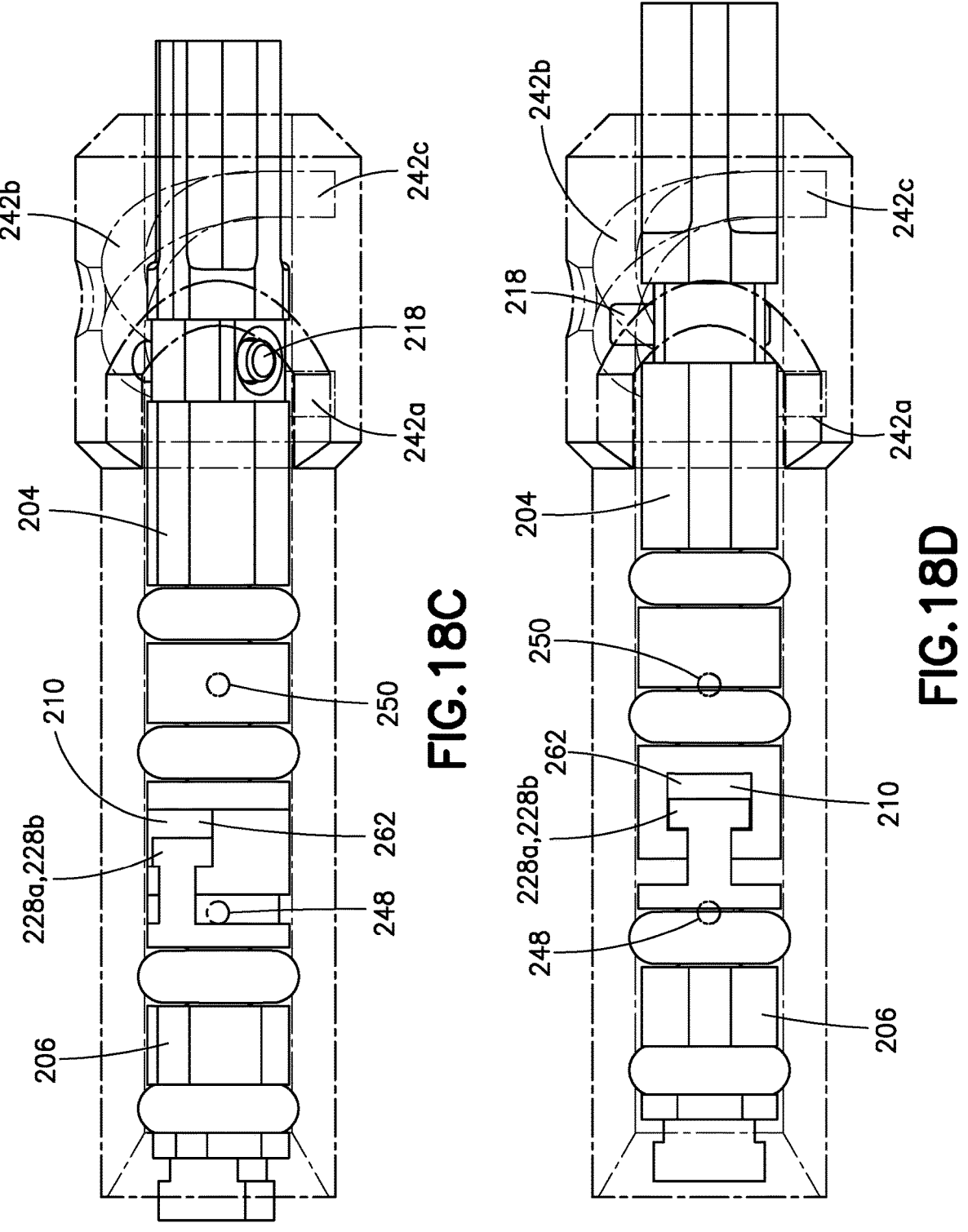

In FIG. 18C, the pin 218 is guided along section 242b of the cam slot 242 during rotation of the piston to cause translation of the piston 204. FIG. 18C depicts the mechanical limit or extreme of the plug flanges 228a,b contacting the proximal side of the notch region 210. The shape 242b of the cam slot causes the plug 206 to overcome seal friction and overcome lag to move with the piston 204 toward the patient port 250.

Figures 18E, 18F:
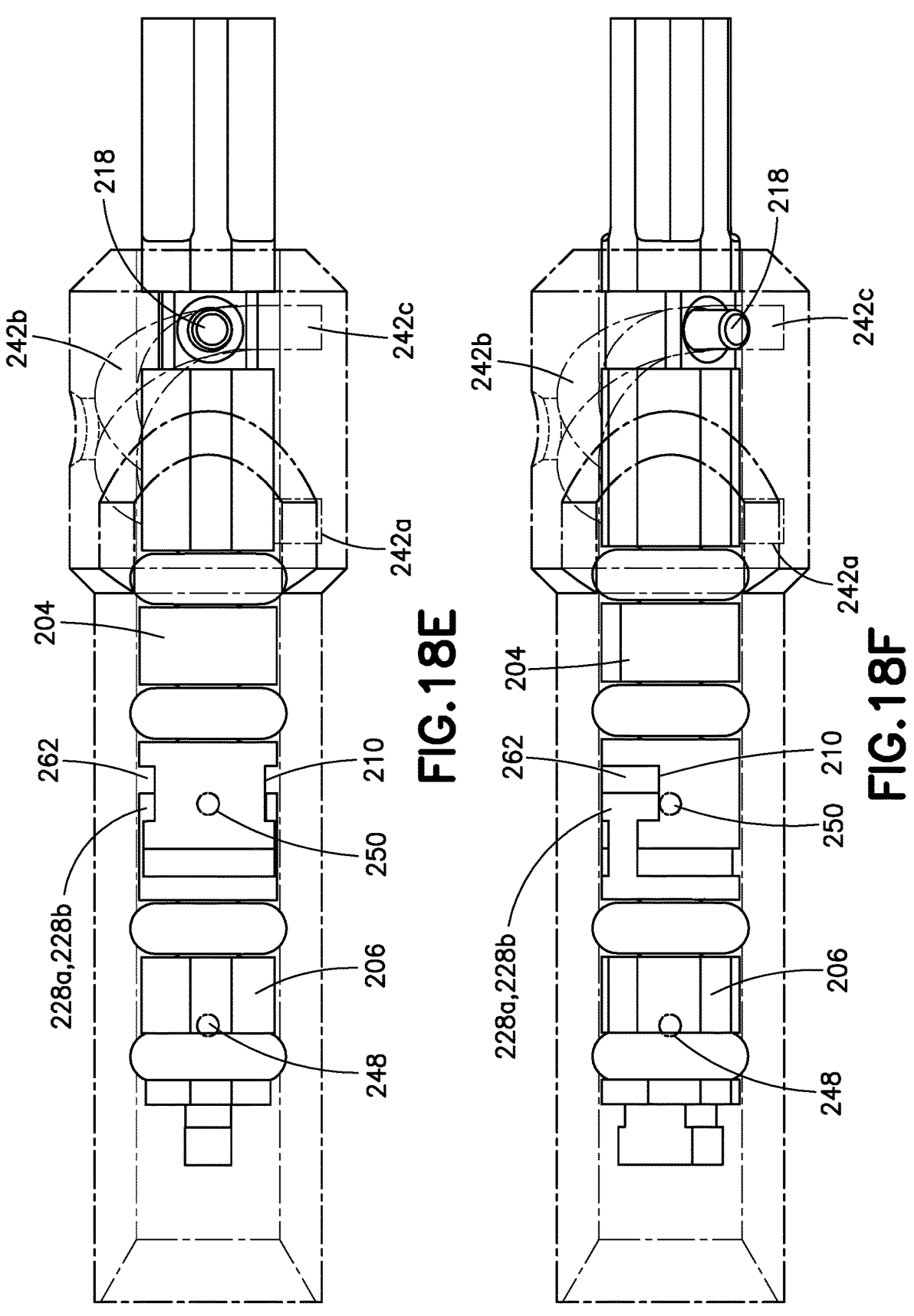
Figures 18G, 18H:
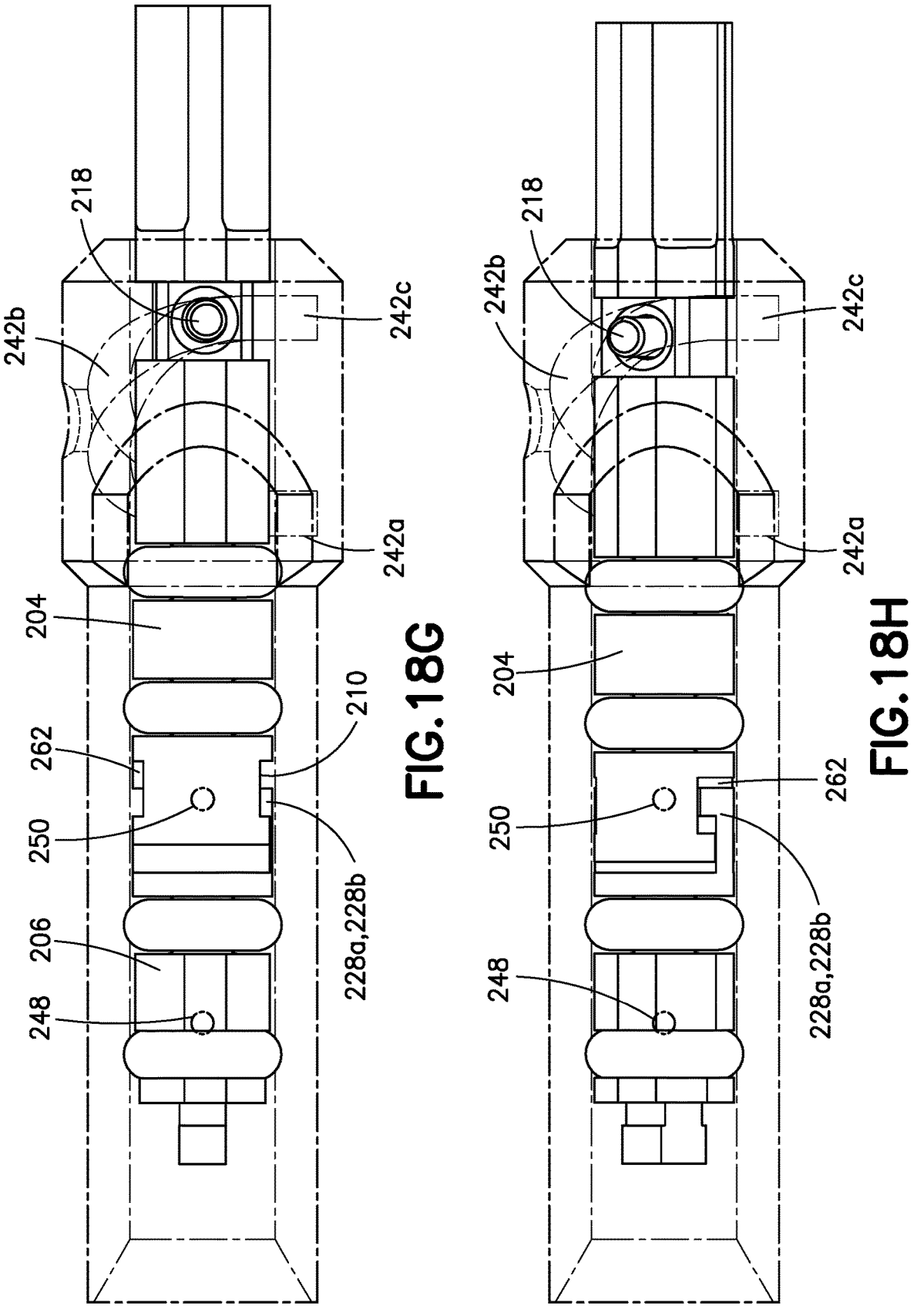

In FIG. 18D, the pin 218 is guided along section 242b of the cam slot 242, causing rotation and translation of the piston 204 and the plug 206 toward the patient port 250. As the pin 218 reaches the end of section 242b of the cam slot 242, as shown in FIG. 18E, the piston 204 and plug 206 rotate but translation stops. The patient 250 port is now aligned with the fluid chamber 262. The pin 218 travels toward the end 242c of the cam slot, as shown in FIG. 18, causing the piston 204 and the plug 206 to rotate. At the end 242c of the cam slot, rotation of the piston 204 can be reversed and the piston 204 and plug 206 turn clockwise, for example.

Figures 18I, 18J:
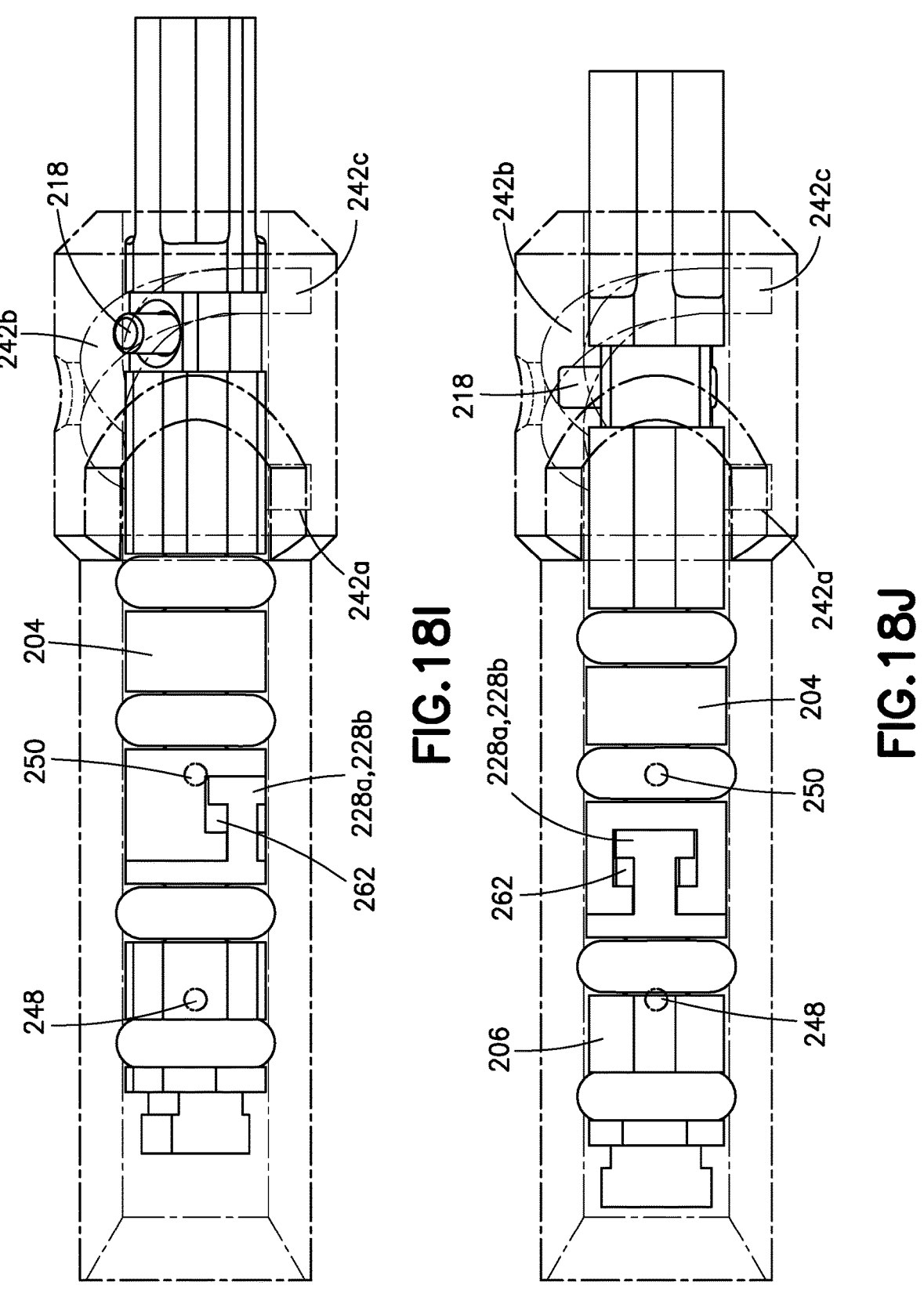

As shown in FIGS. 18G through 18J, the pin 218 is guided toward the section 242b of the cam slot 242 as the piston 204 and the plug 206 rotate. The plug 206 does not translate, but rather only rotates. The piston 204's proximal end 204a pushes toward distal end 206b of plug causing positive pressure in chamber 262 to push fluid out through the patient port 250 toward the patient during a discharge stroke of the pump cycle. FIGS. 18I and 18J illustrate the discharge stroke completion after which the piston 204 and plug 206 being rotating and translating together toward the reservoir port 248 due to the curvature and length of the portion 242b of the slot 242 to guide the pin 218 and the mechanical limits of the plug 206 achieved by the piston proximal end 204a pushing against plug distal end 206b.

Figures 18K, 18L:
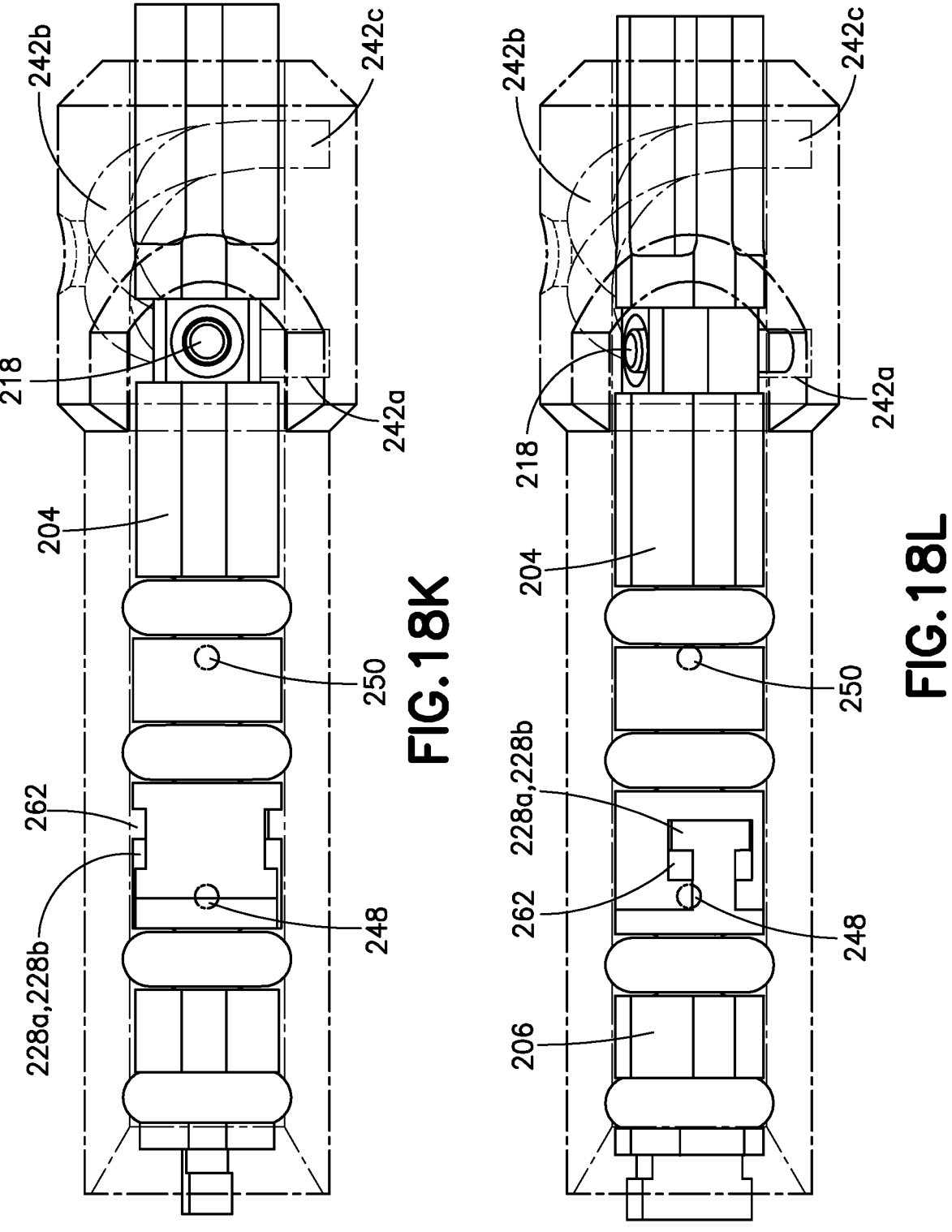

FIGS. 18J and 18K illustrate the chamber 262 moved toward the reservoir port 248 for another intake stroke. As illustrated in FIG. 18L, the pin 210 is in portion 242a of the cam slot 242. The piston 204 and the plug 206 rotate only (e.g., clockwise) and do not translate until the pin 218 contacts the end of the cam slot 242. Piston 204 rotation can be reversed (e.g., by the gearbox or other actuator 134) to commence another intake whereby the piston 204 initially pulls away from the plug 206, and plug friction causes the plug 206 to lag in its translation relative to the piston to cause negative pressure in the chamber 262 and the drawing of fluid into the chamber via the reservoir port 248.

While FIGS. 18A through 18L illustrate a pump cycle comprising an intake stroke and a dispense stroke wherein the direction of piston 204 rotation is reversed, it is to be understood that the pump sub-system 200 can be configured to operate in a single direction of rotation, which can simplify electronics of the pump actuator 134 and possibly reducing battery 162 consumption. The pump sub-system 200 can also be driven with linear actuation as opposed to rotation.

An advantage of the pump sub-system 200 is that the timing of pump chamber 262 exposure to the ports 248 and 250 is mechanically accomplished in a manner that makes direct connection between the reservoir and the patient not possible. When the pump chamber 262 is exposed to the patient side via the port 250 and the piston 204 is fully retracted, the pumping action begins. The plug 206 friction can hold the plug 206 in place, even against backpressure up to 30 psi (e.g., with selected O-ring 234a,b—to—pump housing 208 interference, and therefore friction) until the piston 204 motion overcomes the plug 206 resistance force. At that point, the piston 204 starts pushing forward and expelling fluid from the movable pump chamber 262 toward the patient. When the dispense stroke is complete, the piston 204 bottoms out on the plug 206 and pushes it forward to complete the pump cycle, During all of this, the piston 204 and plug 206 rotate together by means of the interlock mechanism.

The pump sub-system 200 is advantageous because its pump height is significantly reduced (e.g., as compared to the metering subsystems described in WO 2015/157174, which use a manifold with valves apart from a pump housing to direct fluid into and from the reservoir and patient ports, respectively), which allows more space for other components. Further, the pump sub-system 200 obviates need for a manifold seal and sleeve interface and therefore minimizes any likelihood of insulin degradation for fast-acting, less stable insulins, which enables the pump sub-system 200 to be suitable for use with many types of insulin.

The pump sub-system 200 is also advantageous because it allows sufficiently small dose volumes to be delivered, thereby enabling its use as a Type 1 Diabetes pump as well as a solution for other drug therapies.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of claims exemplified by the illustrative embodiments by programmers skilled in the art to which the illustrative embodiments pertain. Method steps associated with the illustrative embodiments can be performed by one or more programmable processors executing a computer program, code or instructions to perform functions (e.g., by operating on input data and/or generating an output). Method steps can also be performed by, and apparatus of the illustrative embodiments can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitr.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of claims exemplified by the illustrative embodiments. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims,

The invention claimed is:

1. A fluid delivery device comprising;
a housing;
a piston configured to be controllably translated within the housing;
a plug having a distal end thereof connected to a proximal end of the piston, the plug being configured to translate within the housing;
wherein the proximal end of the piston is configured with a region therein that defines a telescopic fluid chamber in which the distal end of the plug can translate relative to the piston to permit fluid to flow into the fluid chamber and to discharge fluid from the fluid chamber; and
further comprising an interlock mechanism between the housing and the piston comprising an arcuate cam slot in one of the housing and the piston, and a pin on the other one of the housing and the piston that is configured to engage with the cam slot;
wherein, when the piston is rotated, the cam slot is configured to control a distance along which the piston translates relative to the housing.

2. The fluid delivery device of claim 1, wherein the housing comprises a reservoir port through which fluid is introduced into the housing and a patient port through which fluid is discharged from the housing.

3. The fluid delivery device of claim 2, wherein the piston is controllably translated to align the fluid chamber with the reservoir port during an intake operation of the fluid delivery device, and to align the fluid chamber with the patient port during a discharge operation of the fluid delivery device.

4. The fluid delivery device of claim 3, wherein the plug and the piston are each provided with a seal, and the respective seals are configured to confine fluid in the fluid chamber between the seals.

5. The fluid delivery device of claim 1, wherein the plug is configured with a frictional engagement relative to the housing that provides an amount of friction to cause translation of the plug to lag relative to the piston until the amount of friction is overcome by translation of the piston.

6. The fluid delivery device of claim 5, wherein the distal end of the plug translates between two end stop positions within the piston region, when the distal end of the plug reaches one of the two end stop positions, the amount of friction is overcome and the plug translates with the piston relative to the housing.

7. A fluid delivery device comprising;

a housing;

a piston configured to be controllably translated within the housing;

a plug having a distal end thereof connected to a proximal end of the piston, the plug being configured to translate within the housing;

wherein the proximal end of the piston is configured with a region therein that defines a telescopic fluid chamber in which the distal end of the plug can translate relative to the piston to permit fluid to flow into the fluid chamber and to discharge fluid from the fluid chamber;

wherein the housing comprises a reservoir port through which fluid is introduced into the housing and a patient port through which fluid is discharged from the housing;

wherein the piston is controllably translated to align the fluid chamber with the reservoir port during an intake operation of the fluid delivery device, and to align the fluid chamber with the patient port during a discharge operation of the fluid delivery device wherein the plug and the piston are each provided with a seal, and the respective seals are configured to confine fluid in the fluid chamber between the seals; and wherein the plug is configured with a frictional engagement relative to the housing that provides an amount of friction to cause translation of the plug to lag relative to the piston until the amount of friction is overcome by translation of the piston, and the seal on the piston is configured to contribute to the amount of friction.

8. The fluid delivery device of claim 7, further comprising an interlock mechanism between the housing and the piston comprising an arcuate cam slot in one of the housing and the piston, and a pin on the other one of the housing and the piston that is configured to engage with the cam slot;

wherein, when the piston is rotated, the cam slot is configured to control a distance along which the piston translates relative to the housing.

9. The fluid delivery device of claim 7, wherein the distal end of the plug translates between two end stop positions within the piston region, when the distal end of the plug reaches one of the two end stop positions, the amount of friction is overcome and the plug translates with the piston relative to the housing.

\* \* \* \* \*